(12) United States Patent
Nazareth et al.

(10) Patent No.: US 9,678,070 B2
(45) Date of Patent: Jun. 13, 2017

(54) METHOD AND APPARATUS FOR ELECTROCHEMICAL DETECTION

(71) Applicant: Church & Dwight, Co., Inc., Princeton, NJ (US)

(72) Inventors: Albert R. Nazareth, Mercerville, NJ (US); Shang Li, Princeton Junction, NJ (US); Giles H. W. Sanders, Hertfordshire (GB); Anthony Edward George Cass, Hertfordshire (GB); Marian Rehak, Cambridge (GB)

(73) Assignee: Church & Dwight Co., Inc., Princeton, NJ (US)

( * ) Notice: Subject to any disclaimer, the term of this patent is extended or adjusted under 35 U.S.C. 154(b) by 93 days.

(21) Appl. No.: 14/699,063

(22) Filed: Apr. 29, 2015

(65) Prior Publication Data
US 2016/0320383 A1     Nov. 3, 2016

(51) Int. Cl.
*G01N 33/558*   (2006.01)
*C12Q 1/00*   (2006.01)
*C12Q 1/58*   (2006.01)
*G01N 33/543*   (2006.01)

(52) U.S. Cl.
CPC ........... *G01N 33/558* (2013.01); *C12Q 1/001* (2013.01); *C12Q 1/58* (2013.01); *G01N 33/543* (2013.01); *G01N 2458/30* (2013.01)

(58) Field of Classification Search
None
See application file for complete search history.

(56) References Cited

U.S. PATENT DOCUMENTS

| | | | |
|---|---|---|---|
| 8,211,711 B2 | 7/2012 | Nazareth et al. | |
| 8,268,636 B2 | 9/2012 | Nazareth et al. | |
| 8,951,395 B2* | 2/2015 | Machida | G01N 27/3272 204/403.01 |
| 2012/0083044 A1 | 4/2012 | Sturman et al. | |
| 2014/0248642 A1* | 9/2014 | Cass | G01N 33/5438 435/7.92 |

FOREIGN PATENT DOCUMENTS

| | | | | |
|---|---|---|---|---|
| GB | WO 2013011323 A2 * | 1/2013 | ......... | G01N 33/5438 |
| WO | 2006103450 A2 | 10/2006 | | |
| WO | 2013011323 A2 | 1/2013 | | |

* cited by examiner

*Primary Examiner* — Chris L Chin
(74) *Attorney, Agent, or Firm* — Church & Dwight Co., Inc.

(57) ABSTRACT

The invention provides an apparatus and methods for the electrochemical detection and/or quantitation of an analyte in a sample, wherein the device comprises a substrate and a detector, wherein the substrate comprises a labeled binding agent, wherein the label is an enteric material particle that encapsulates a ferrocene methanol redox species.

14 Claims, 7 Drawing Sheets

METHOD AND APPARATUS FOR ELECTROCHEMICAL DETECTION

BACKGROUND OF THE INVENTION

Field of the Invention

Certain aspects of the present invention generally relate to devices and methods for the electrochemical detection and quantitation of analyte in a sample.

Background

Point of care (POC) diagnostic tests are convenient and inexpensive devices useful for the detection of a target molecule, in a sample. POC tests are employed in a variety of settings, including for medical, consumer, or environmental purposes because of the low cost, ease of use, and, portability that they afford. POC tests have become increasingly popular in part because of the rapidity with which results are achieved and for the flexibility of configuring the devices for a variety of applications.

The lateral flow assay (LFA) is a POC diagnostic tool that is capable of determining the presence or absence of an analyte, typically, through visual observation of a discernible color change. One common example of such LFA tests is the conventional household pregnancy test. LFAs generally involve the use of a labeled antibody deposited at a first position on a solid substrate. Sample is applied to the first position, causing the labeled antibody to reconstitute in solution, whereupon the antibody binds to complementary analyte in the sample. Alternatively, labeled antibody is mixed with the sample prior to application on the LFA. In either case, a complex of analyte and antibody forms. The analyte-antibody complex flows along the liquid front from the first location through the solid substrate to a second location, a test line, where an immobilized antibody is located. The immobilized antibody captures the analyte through specific interaction, resulting in a high concentration of labeled antibody at the test line. The high concentration of labeled antibody provides a detectable visual signal. Gold nanoparticles are typically used to label the antibodies because they are relatively inexpensive and provide easily observable color indications based on the surface, plasmon resonance properties of gold nanoparticles. In many cases, this signal is used to, provide only, qualitative, information, such as whether or not the analyte is present in the sample.

FIGS. 1A and 1B depict a conventional one-step sandwich LFA 12, as described in the prior art. The sandwich LFA 12 is comprised of a substrate 13 over or through which the liquid sample flows. The sandwich LFA 12 comprises an upstream region 15 and a downstream region 17. Deposited on the substrate 13 at a first, region 14 are antibodies 24 conjugated to a visually or optically detectable particle 25, such as a gold nanoparticle. When a sample is applied to the upstream region 15 of the substrate 13, it may, flow over or through the substrate 13 to the downstream region 17 of the substrate 13. The labeled antibodies are reconstituted by the sample liquid when the sample flows to and through the first region 14. The labeled antibodies are reactive to a first epitope on an analyte of interest 27 which may be present in the sample, such that the labeled antibodies bind the analyte 27 when the sample passes through the first region 14.

The substrate 13 also comprises a second region 16, where capture antibodies 26 are deposited. The capture antibodies 26 are solubilized by the sample when the sample flows to and through the second region 16. The capture antibodies have biotin 29 conjugated thereto, and are reactive to a second, different epitope on the antigen 27, such that the capture antibodies 26 also bind to the analyte 27 when the analyte 27 passes through the second region 16. The analyte 27 is therefore bound by both the labeled antibodies 24 and the capture antibodies 26, forming a "sandwich" complex. The sandwich complex flows with the sample to a third region 18 forming a test line. The third region 18 has avidin 28 immobilized thereon. The avidin 28 binds to the biotin 29 on the capture antibodies 26, thereby retaining the sandwich complex at the third region 18, resulting in the accumulation of label particles 25 at the third region 18, which provides for a visual determination of the presence of analyte 27 in the sample. Although this sandwich detection method has been widely used, it is also possible to immobilize the capture antibodies 26 at the third region 18 for trapping labeled antibody-antigen complexes at the third region 18, and eliminating the second region 16.

Labeled antibodies 24 that are not bound to analyte 27 continue to flow past the third region 18 to an optional fourth region 20 forming a control line. The fourth region 20 has immobilized antibodies deposited thereon which bind to the labeled antibodies (e.g. species specific antibodies). Thus, when the analyte of interest 27 is present in the sample, a visual signal may be detected both at the third region 18 and at the fourth region 20. However, if the analyte 27 is not present in the sample, a visual signal is detected only at the fourth region 20.

FIG. 1B is a schematic representation of the binding interactions that take place at the third region 18. Labeled antibodies bind to a first epitope on the analyte 27 in the sample. Capture antibodies 26 with biotin 29 conjugated thereon binds to a second epitope on the analyte 27, forming the sandwich complex. Avidin 28 is immobilized on the third region 18, and bind to the biotin that is conjugated to the capture antibodies 26. The result is the capture of the sandwich complex, thereby providing the visual signal indicating the presence of the analyte 27 in the sample.

Recent efforts in the field of LFAs have focused on creating devices capable of quantitating the amount of analyte present in the sample. Such information is important, for example, when the amount of analyte in sample, rather than merely its presence, provides the required information. For example, a baseline level of analyte may be normal, but elevated analyte may be indicative of disease when it exceeds some threshold level.

SUMMARY OF THE INVENTION

Various implementations of systems, methods and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In one implementation, a diagnostic device for detection of analyte in a sample comprises a substrate comprising a first region comprising labeled antibodies deposited thereon, wherein the labels of the labeled antibodies comprise enteric material particles with ferrocene methanol embedded therein. The substrate also comprises a second region comprising an enzyme deposited thereon, wherein the enzyme interacts with a chemical during the detection process to cause the release of ferrocene methanol from enteric material particles located in the second region. The device also comprises a detector configured to detect released ferrocene methanol.

In another implementation, a method of making an assay device comprises mixing an enteric material with ferrocene methanol in a solvent, removing the solvent to form particles of enteric material having ferrocene methanol embedded therein, attaching antibodies to the beads by physical adsorption or other means to produce labeled antibodies, and depositing the labeled antibodies onto a first region of a substrate.

In another implementation, a label for biochemical assays comprises an enteric material particle having ferrocene methanol embedded therein.

In another implementation, a method for determining the presence and quantity of analyte in a urine sample comprises applying urine to a first region of a substrate, reconstituting labeled antibodies at a first region of the substrate with the urine, wherein the label of the labeled antibodies comprises an enteric material particle having ferrocene methanol embedded therein, solubilizing urease at a second region of the solid matrix with the urine to release ferrocene methanol into the urine from labelled antibodies trapped at the second region of the substrate, and detecting the released ferrocene methanol at the second region of the substrate.

Other aspects of the invention will become apparent by consideration of the detailed description and accompanying drawings.

BRIEF DESCRIPTION OF THE DRAWINGS

In addition to the features mentioned above, other objects and advantages of the invention will be readily apparent from the following descriptions of the drawings. To provide a better understanding of the advantages, aspects, and features of the invention, the following drawings are provided. It should be understood that these drawings depict typical embodiments, and are not intended to be limiting in scope.

DETAILED DESCRIPTION OF PREFERRED EMBODIMENTS

Figure 1B:
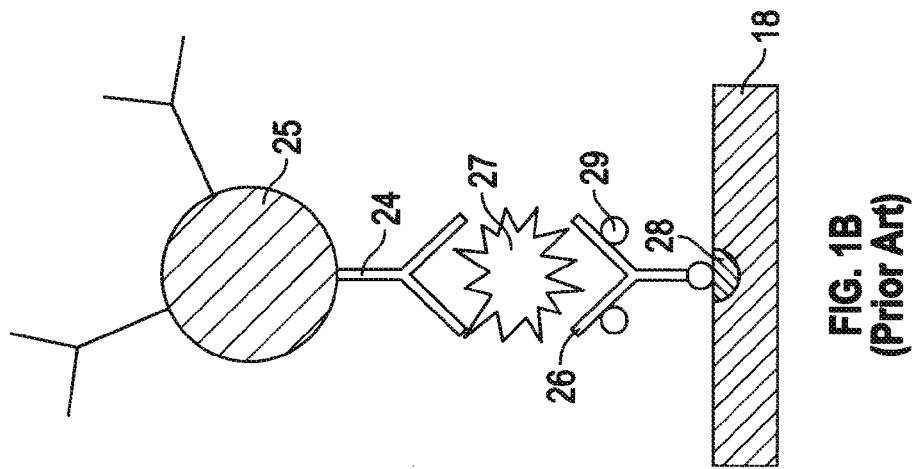
FIG. 1B is a schematic representation of the binding interaction that takes place between the antibody and analyte on the lateral flow assay, as described in the prior art.

The devices and methods described herein comprise a device for the detection and quantitation of analyte in a sample through electrochemical detection of releasable ferrocene methanol. The present invention increases the sensitivity of detection and provides a quantitative readout of the amount of target analyte, while retaining the simplicity of typical POC test devices.

Various aspects of the novel systems, apparatuses, and methods are described more fully hereinafter with reference to the accompanying drawings. The disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the novel systems, apparatuses, and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different point of care devices, some of which are illustrated by way of example in the figures and in the following description of the preferred aspects. The detailed description and drawings are merely illustrative of the disclosure rather than limiting, the scope of the disclosure being defined by the appended claims and equivalents thereof.

One proposed means of quantitating analyte using LFAs is by using redox active species that are associated with a conjugate molecule. When the conjugate binds to the analyte, the redox species is carried to the detection zone, where the species is cleaved. The cleaved species is detected by a detector through electrochemical means. The detector provides some numerical readout indicating the amount of cleaved redox species, which is used to determine the quantity of analyte in the sample. The resulting electrochemical signal is proportional to the concentration of analyte present at the detection zone.

WO2006/103450 provides a quantitative detection device and method that uses cleavable redox species. The redox cleavable species described therein include ferrocene derivatives, which are coupled to a particle, which in turn, is coupled to an antibody. The ferrocene derivatives are coupled to the exterior of the particle through aldehyde-, carboxylic acid-, or amino-modification of the particle. Alternatively, the ferrocene derivatives are attached to the exterior of the particle through polymer chains that carry functional groups that allow attachment of the cleavable species to the particle. The cleavable species can be cleaved by UV or with the addition of acid. Upon cleavage, the cleaved redox species is detected by the detector through electrochemical means, and the presence or amount of analyte is determined. Another proposed method using liberated redox species is proposed in WO 2013/011323. In this document, a redox species is released from the matrix of a polymer particle at the test line. The polymer containing the redox species can be dissolved to release the redox species by creating an alkaline local environment with enzymes deposited at the test line that react with compounds in the sample.

Figure 2B:
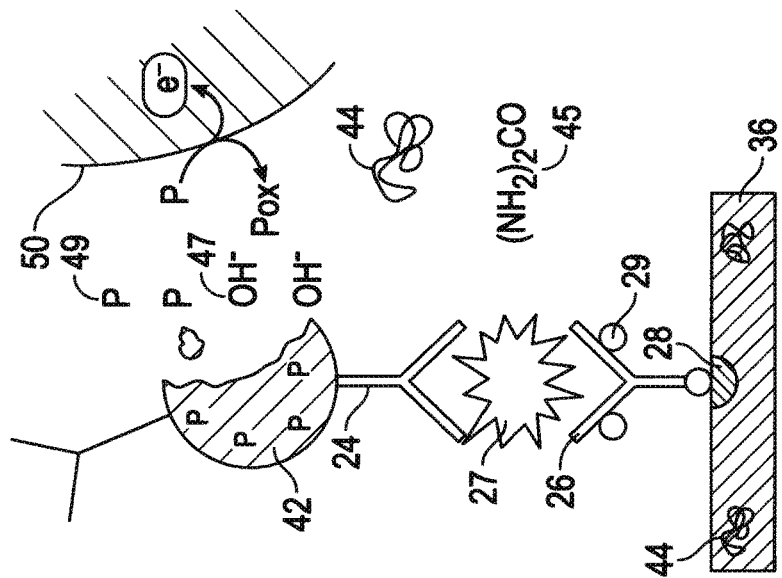
FIG. 2B is a schematic representation that depicts the binding interaction between the antibody and analyte. This representation also depicts the interaction of the substrate with the enzyme, which causes a local increase in the pH, resulting in the release of FeMe from the polymer bead and subsequent detection at an electrode.
Figure 2A:
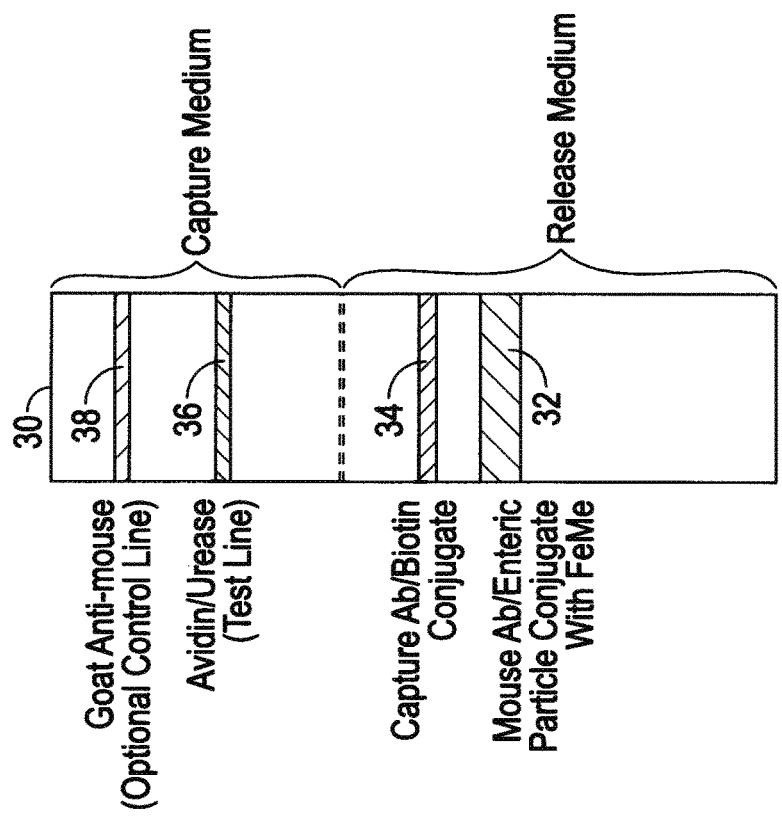
FIG. 2A is a schematic representation of an exemplary electrochemical lateral flow assay in accordance with embodiments described herein.

FIG. 2A is a schematic representation of an exemplary electrochemical LFA in accordance with embodiments described herein. The LFA is comprised of a substrate 30 through or over which the liquid sample flows. This substrate 30 may comprise any suitable solid material or membrane, such as porous and/or non-porous substances over or within which sample can flow such as silicon, silicon oxide, metallic and metal-coated surfaces, polymeric, and polysaccharide surfaces. Such surfaces can include, for example, cellulose, nitrocellulose, cellulose acetate, polyacrylamide, agarose polyacrylamide, polymers, agarose, starch, nylon, nylon polyesters, dextran, cross-linked dextran, dextran acrylamide copolymer, cross-linked hydroxymethylmethacrylate, substituted cross-linked polystyrenes, polyvinylalcohol, wool, metal oxides, porous ceramics coated with hydrophilic organic polymers, and glass.

The substrate 30 comprises a first region 32, a second region 34, and a third region 36. The first region 32 has labeled antibodies deposited thereon. The labeled antibodies are labeled with a particle 42 (also referred to herein as a bead) having a redox species embedded therein, where the redox species can be oxidized and reduced at an electrode surface so as to be usable for electrochemical detection. The particles are capable of releasing the encapsulated redox species when subjected to a pH change, typically under alkaline conditions. A wide variety, of materials, referred to herein as enteric materials, that dissolve under elevated pH are known, and have been used as coatings for pharmaceuticals to coat the active ingredient such that it isn't released in the acid environment of the stomach, but then dissolve to release the active ingredient in the more alkaline environment of the small intestine. These materials include various fatty acids, waxes, shellacs, synthetic polymers, and plant fibers. A wide variety of redox species are also known and used in a variety of different electrochemical detection applications. Ferrocene and derivatives thereof are one example, but many others have been used and proposed.

Although ferrocene derivatives have been used as redox species for electrochemical detection, prior work has been unable to employ certain ferrocene derivatives as the redox species in LFA applications, because various inherent characteristics of ferrocene derivatives make many of them difficult and/or unreliable to employ in LFA systems. For example, WO2006/103450 teaches against the use of ferrocene methanol because it was shown to bind to human serum albumin (HSA) to a large extent, thereby limiting the ability of some assays to differentiate between the analyte of interest and competitive binding through non-specific interactions.

Furthermore, the inventors have found that ferrocene derivatives are difficult to select and employ in LFA devices using enteric material entrapped redox species because of their hydrophilicity/hydrophobicity and resultant inability to adequately solubilize both in solution and in an enteric material. For example, hydrophobic ferrocene derivatives can be employed when they are entrapped within a polymer carrier that can transport the ferrocene derivative to the detection site, but the ability to transport the entrapped ferrocene derivative is not the sole concern, because the ferrocene derivative also needs to be efficiently released to the aqueous solution from the polymer at the appropriate time This is an important consideration when attempting to implement a system that incorporates a redox couple into polymer beads for delivery to a test line.

Thus, in order to have adequate entrapment of the redox couple within the polymer beads, the redox couple must be adequately hydrophobic. However, if the redox material is excessively hydrophobic, then upon release from the enteric material, the redox species will not dissolve in the aqueous phase to allow for electrochemical detection by the electrode. Therefore, the redox species should exhibit a proper balance of hydrophobic and hydrophilic properties, wherein the redox couple is sufficiently hydrophobic for efficient entrapment within the enteric material, but sufficiently hydrophilic to dissolve in the aqueous phase. Additionally, the redox couple should possess adequate electroactivity in order to create accurate and consistent signal with the electrode. Taking this into account, it was discovered through extensive research that ferrocene methanol (sometimes denoted FeMe herein) is an especially advantageous redox species of choice for such LFA applications, because it has a good hydrophobic to hydrophilic balance providing for both high entrapment efficiency as well as high release efficiency after bead dissolution. In addition, FeMe is electrosensitive, has extended stability in solution, and is not light sensitive. Furthermore, FeMe undergoes fast, preferably diffusion limited, electron exchange at, the detector.

Also important for the efficacy of the current invention is a particle comprised of appropriate enteric material. The bead material must be able to efficiently entrap the FeMe, but also be able to respond to specific stimuli, thereby releasing FeMe at the appropriate location (for example, near the detector). A copolymer of methyl methacrylate and methacrylic acid is one such appropriate polymer because it has hydrophilic/hydrophobic properties capable of efficiently entrapping FeMe, but it will dissolve when a pH change takes place, such as the pH change that takes place near the detector as described herein. Mixtures of enteric material that include a copolymer of methyl methacrylate and methacrylic acid may be, used in some embodiments. The polymer may advantageously be mostly a copolymer of methyl methacrylate and methacrylic acid (e.g. more than 75%), and the inventors have achieved good results with polymer consisting essentially of a copolymer of methyl methacrylate and methacrylic acid such that the only other constituents are potentially small amounts of impurities or other ingredients that do not change the characteristics of the polymer significantly from a polymer consisting solely of a copolymer of methyl methacrylate and methacrylic acid, which may also be utilized.

Therefore, the inventors have found that an especially advantageous labeled antibody is an antibody against the analyte of interest that is conjugated to particles 42 comprising a copolymer of methyl methacrylate and methacrylic acid having FeMe encapsulated therein. This labeled antibody binds to a first epitope on the analyte, and this complex travels with the liquid front over or through the substrate 30 through from the first region 32 where the labeled antibody is solubilized, to a second region 34. Capture antibodies 26 having biotin conjugated thereon are deposited at the second region 34 and are also solubilized by the sample. The capture antibody is reactive to a second epitope on the analyte, and binds to the analyte as the analyte passes through the second region 34, forming a sandwich complex. This sandwich complex continues to flow through the solid substrate 30 to a third region 36, where the sandwich complex is captured. As described above, it is also possible to immobilize the capture antibodies 26 at the third region 36 for trapping labeled antibody-antigen complexes at the third region 26, and eliminating the second region 34. Referring now to FIG. 2B, avidin 28 and enzyme 44 are immobilized at the third region 36. The avidin 28 binds to the biotin 29 that is conjugated to the capture antibody 26, resulting in the capture of the sandwich complex. The enzyme 44 deposited at the test line 36 reacts with a chemical 45, resulting in a relative increase of hydroxide ions 47, and a resulting local pH change. This change in pH causes the polymer bead 42 to dissolve, and results in the release of the FeMe (denoted "P") 49. At least one electrode surface 50 is placed within close proximity of the third region 36, and current caused by oxidation/reduction of the redox species is detected. The amount of current, corresponding to the amount of FeMe present enables the ascertainment of the quantity of analyte present in the sample.

The change in pH is advantageously the result of the interaction between a chemical naturally present in the sample and the enzyme 44, although in some embodiments of the invention, the appropriate chemical is added to the sample prior to application to the LFA, or may also be deposited on the substrate 30. For example, the substrate may be deposited in the first region 32 prior to sample application, and dissolve into the solution upon sample application, whereupon it travels with the liquid front to the second region 34 and third region 36.

In some embodiments of the invention, the solid substrate may further comprise a fourth region 38 forming a control line. Antibody is deposited and immobilized at the control line 38, whereupon the antibodies capture excess labeled antibody, thereby providing a control signal as described above.

In the LFA system of FIGS. 2A and 2B, the enzyme 44 is urease, which becomes solubilized by a urine sample at the third region 36. The chemical is urea 45, which is naturally present in the urine sample. The urease converts the urea into ammonia and carbon dioxide, and the free ammonia reacts with the water in the sample to form ammonium hydroxide, raising the local pH in the third region.

In this particular application, the inventors have found FeMe to be especially advantageous because urine samples can naturally contain other redox species which can also produce current signals at the electrode, surface 50. Such naturally present redox species include vitamin C, uric acid, and paracetamol. It has been found by the inventors that the redox potential of FeMe is farther from the redox potentials of these potentially interfering chemicals, and therefore produces more accurate, less noisy measurements of trapped analyte than other ferrocene derivatives such as ferrocene carboxylic acid.

Although only one electrode surface 50 is illustrated in FIG. 2B, there will typically be two electrode surfaces present, a working electrode surface and a reference electrode surface. These electrodes may be carbon or gold films or plates in contact with the substrate 30 in or near the third region 36 on either side of the substrate 30. The inventors have found good electrochemical signals when the electrodes are partially embedded within the material of the substrate 30. For example, the electrode(s) may be formed as wires that pierce and extend transversely through the substrate 30 perpendicular to the major faces of the substrate 30.

A circuit (not shown) may be coupled to the electrodes(s), which may include A/D conversion circuitry and digital processing circuitry to convert measured current into a signal indicative of the presence and/or quantity of analyte in the sample.

EXAMPLES

Encapsulation of FeMe in the Copolymer Particles

Figure 3:
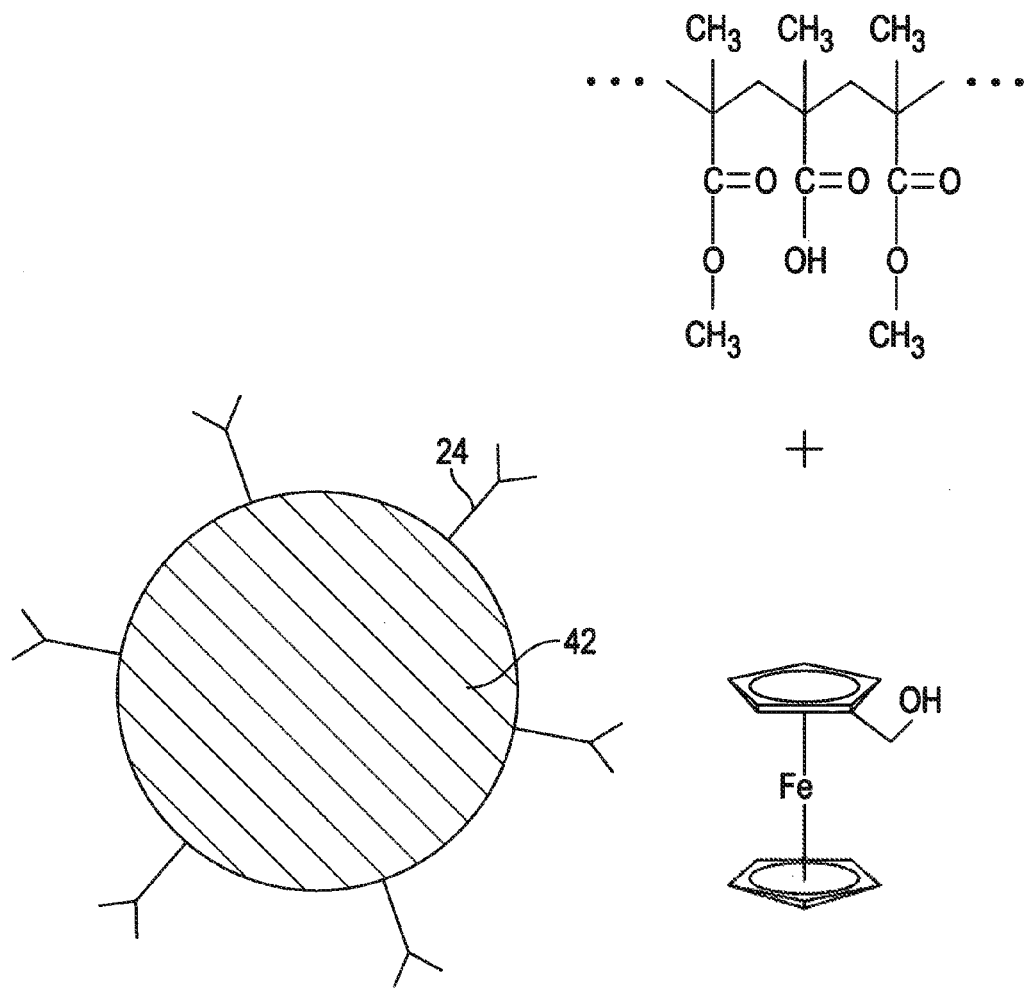
FIG. 3 is schematic representation of labeled antibody, copolymer of methyl methacrylate and methacrylic acid, and ferrocene methanol in accordance with embodiments described herein.

A quasi-emulsion solvent diffusion (QESD) method was used to prepare polymer particles encapsulated with FeMe. Eudragit S100, a copolymer of methyl methacrylate and methacrylic acid was selected to encapsulate FeMe because of its pH dependent dissolution properties in various buffers. Referring now to FIG. 3, the structure of the copolymer of methyl methacrylate and methacrylic acid is depicted. This copolymer is an anionic copolymer with dissolution at about pH 7.0. The copolymer and FeMe were dissolved together in ethanol. An emulsifier was dissolved in pH 5 citrate buffer at a 1% concentration. The polymer solution was added to the emulsifier solution and allowed to stir overnight. The resulting copolymer beads with encapsulated FeMe were centrifuged and washed with pH 5 citrate buffer.

Figure 4A:
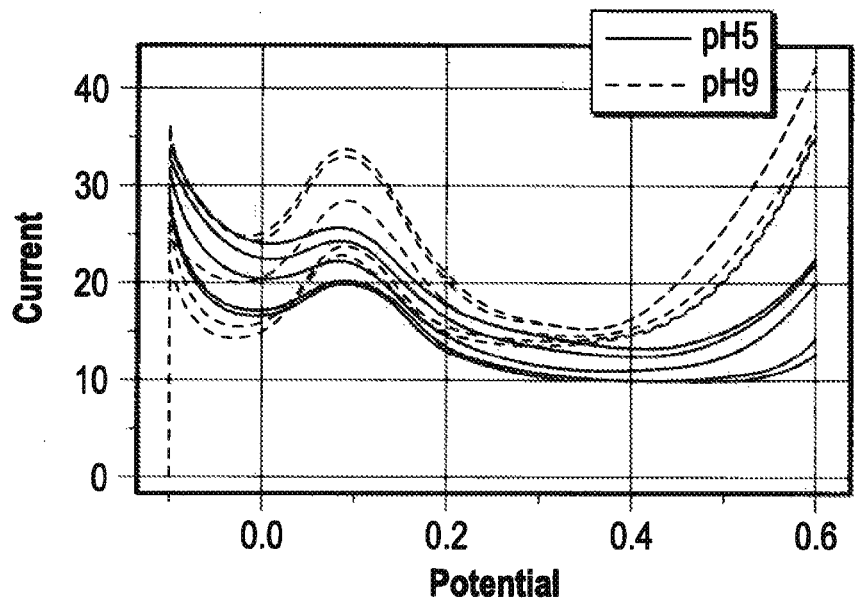
FIG. 4A is a graphical representation of the electrochemistry of dimethylferrocene loaded polymer beads at different pH values.
Figure 4B:
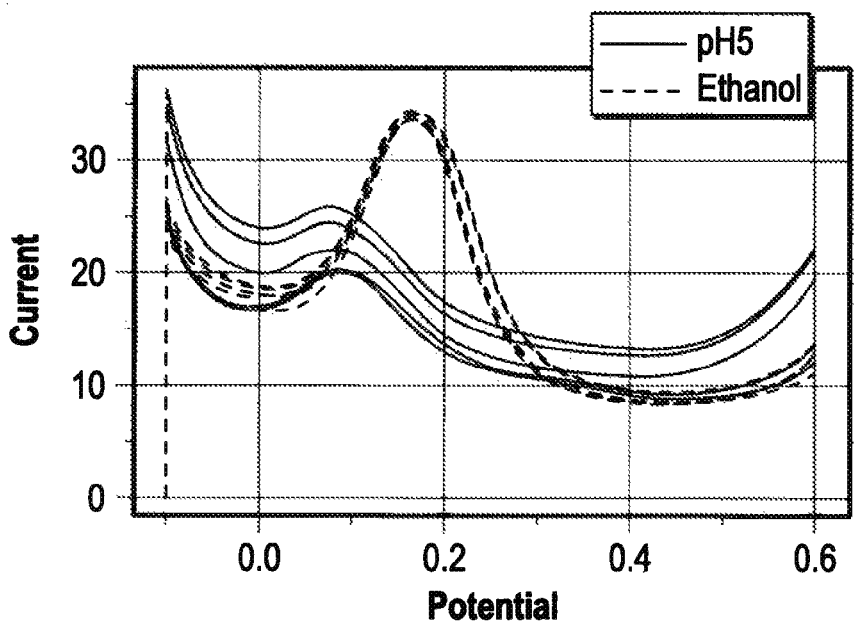
FIG. 4B is a graphical representation of the electrochemistry of dimethylferrocene loaded polymer beads in aqueous solution and in ethanol.

Additional redox species were tested for their efficacy of loading and release from the copolymer beads. FIG. 4A depicts the graphical representation of electrochemical measurements of dimethylferrocene loaded beads. Dimethylferrocene is a hydrophobic molecule that is efficiently entrapped within the copolymer particles. However, no significant difference was observed between the electrochemical measurements at pH 5 (solid lines) and identical measurements at pH 9 (dashed lines), indicating that although the copolymer particles dissolve in pH 9, dimethylferrocene does not solubilize in the aqueous phase at pH 9, and no appreciable signal is detected. On the other hand, when the beads are dissolved in ethanol, dimethylferrocene solubilizes in the ethanol, and a signal is detected (FIG. 4B, dashed lines). However, although detection of the redox species was observed in an ethanol solution, ethanol is incompatible with the LFA technology for its typical use with aqueous samples.

Figure 5A:
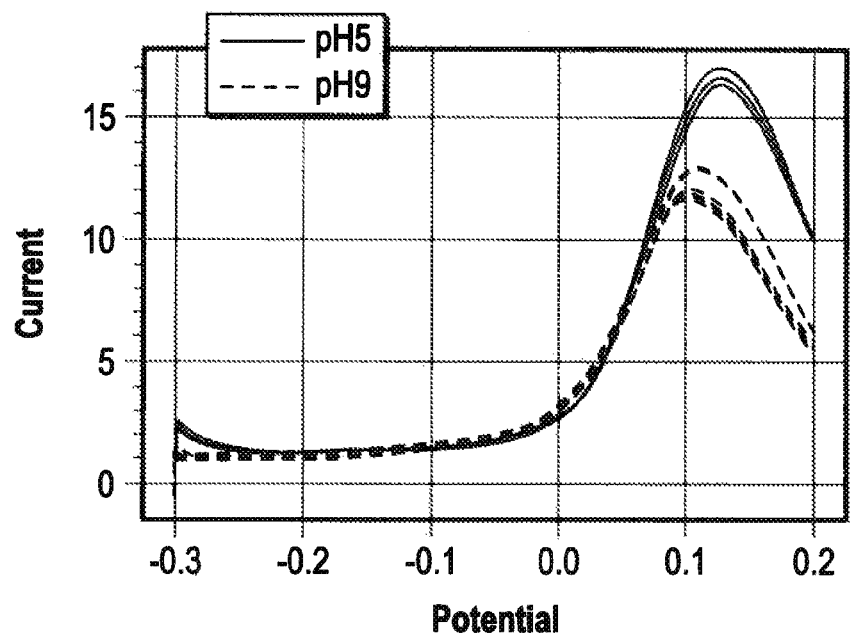
FIG. 5A is a graphical representation of the electrochemistry of tetrathiafulvalene loaded polymer beads at different pH values.
Figure 5B:
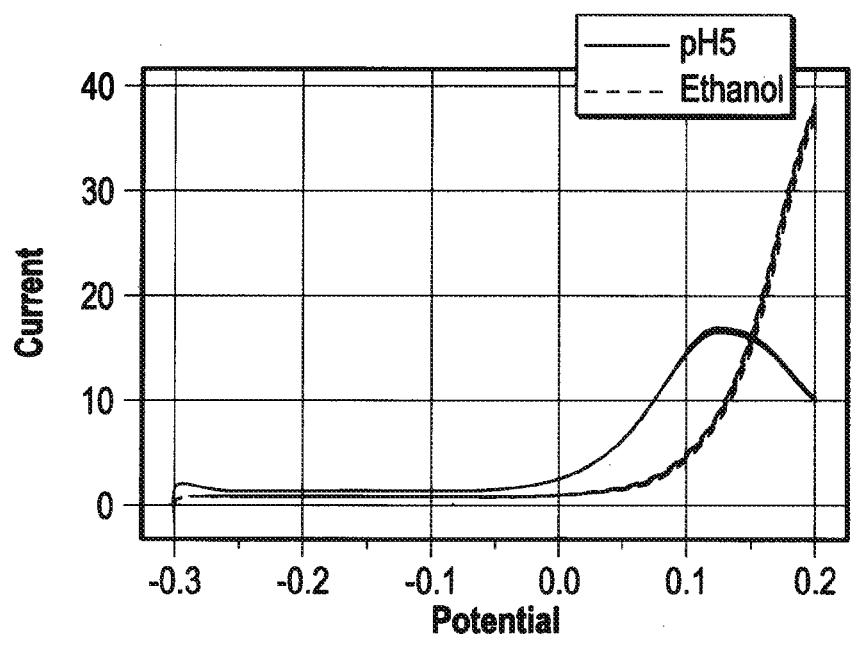
FIG. 5B is a graphical representation of the electrochemistry of tetrathiafulvalene loaded polymer beads in aqueous solution and in ethanol.

Similarly, FIGS. 5A and 5B depict the electrochemical measurements of tetrathiafulvalene loaded beads. Tetrathiafulvalene is a hydrophobic molecule that is efficiently entrapped within the copolymer particles. However, similar to dimethylferrocene, no significant difference was observed between the electrochemical measurements at pH 5 (solid lines) and pH 9 (dashed lines). As observed with dimethylferrocene, the tetrathiafulvalene loaded beads stimulate an electrochemical measurement when dissolved in ethanol.

Figure 6:
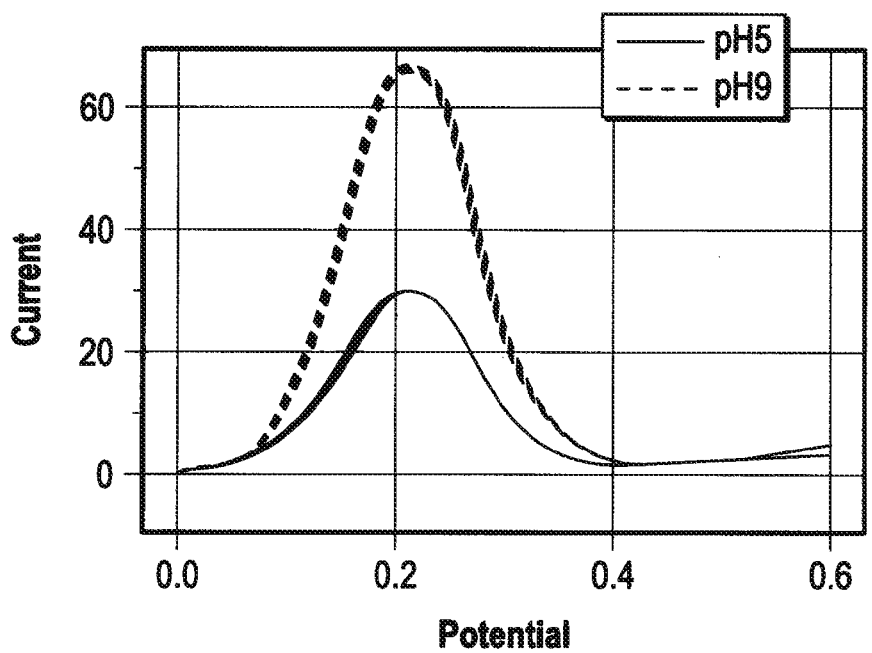
FIG. 6 is a graphical representation of the electrochemistry of ferrocene methanol loaded polymer beads at different pH values.

FIG. 6 depicts the electrochemical measurements of FeMe loaded beads. At pH 5 (solid lines), a small peak is elicited, due to residual FeMe not entrapped within the beads. At pH 9 (dashed lines), a significant difference in electrochemical signal is detected, indicating that the beads dissolved and FeMe solubilized in aqueous solution at pH 9.

Coupling of Antibody to the Copolymer FeMe Loaded Beads

Figure 7:
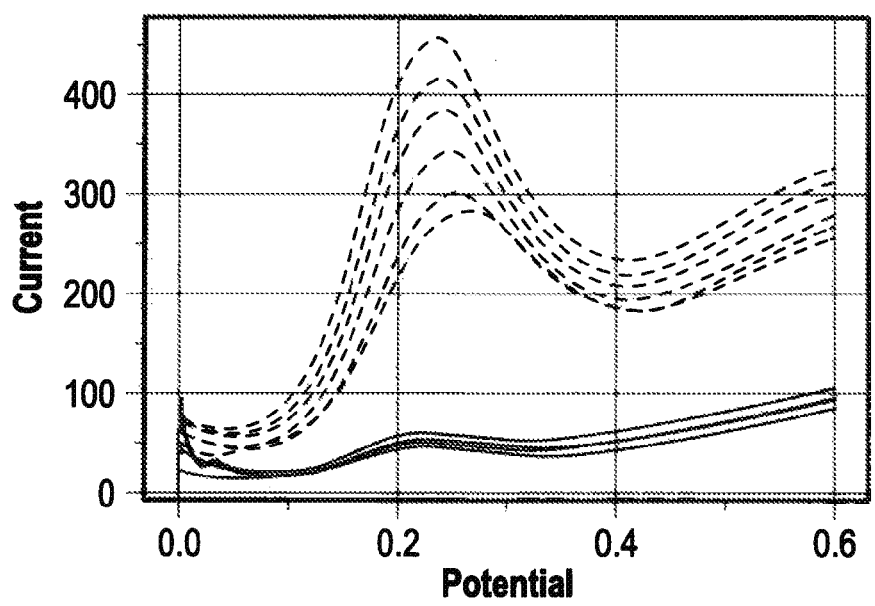
FIG. 7 is a graphical representation of the square wave voltammetry measurement of ferrocene methanol loaded polymer beads dried on nitrocellulose membrane.

The purified beads encapsulating the FeMe were incubated with anti-human chorionic gonadotropin (hCG) monoclonal antibody in 25 mM MES buffer at pH 6.5 at room temperature overnight under mild agitation. The ratio between the beads and the antibody was 10:1 w/w. The resulting labeled antibody is depicted in FIG. 3. The labeled antibodies 42 loaded with FeMe were tested for their efficacy in releasing FeMe when placed on a test strip. FIG. 7 is a graphical representation of the square wave voltammetry used to test the release of FeMe from the labeled antibody. The labeled antibody was dried on a nitrocellulose membrane. A first membrane was subjected to a solution at pH 5 (solid lines) and a second identical membrane was subjected to a solution at pH 9 (dashed lines). At pH 5, the beads did not dissolve, and there was no release of the redox species. At pH 9, the beads dissolved and FeMe was released, resulting in electrochemical detection. The data shows each condition recorded for 6 subsequent runs recorded every minute. At pH 9 the data shows increasing peaks due to bead dissolution and FeMe release.

Detection of Human Chorionic Gonadotropin

Figure 1A:
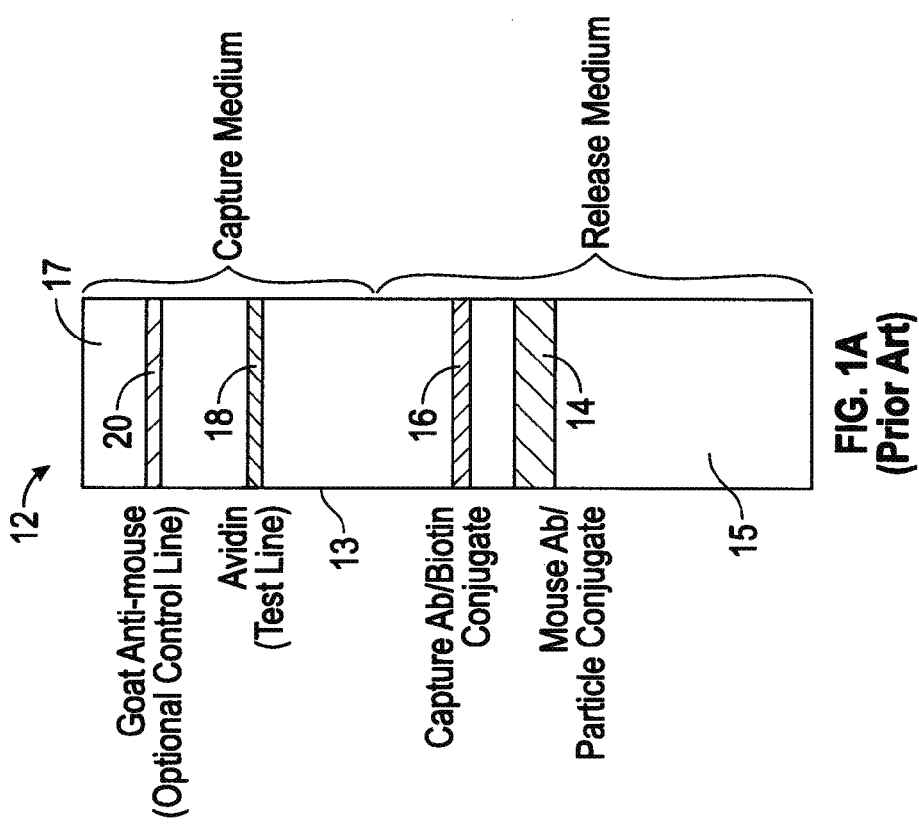
FIG. 1A is a schematic representation of a lateral flow assay strip as described in the prior art.

Human chorionic gonadotropin (hCG) in urine samples is commonly used to determine a woman's pregnant/non-pregnant status. Conventional pregnancy tests use the sandwich LFA as described in FIG. 1A and FIG. 1B. The standard assay employs antibody labeled with gold nanoparticles. The surface plasmon resonance properties of gold nanoparticles enable the user to visualize the location of the antibody. This results in a qualitative determination of whether or not the woman is pregnant based on the visual detection of a signal at the test line.

However, under certain circumstances, it is desirable to determine the quantity of antigen present in the sample as well. The present invention is an amplified electrochemical lateral flow assay, which can provide both qualitative and quantitative results. To demonstrate the principles of the present invention, the detection and quantitation of hCG in a urine sample was carried out. A test strip was provided, as described in FIG. 2A and FIG. 2B. The test strip comprises a biphasic test strip comprising a cellulosic release medium and a nitrocellulose membrane laminated onto a Mylar backing. The cellulosic release medium allows for deposited molecules to mobilize when sample flows through the membrane. The test strip comprises a first region 32, a second region 34, and a third region 36. Deposited on the first region 32 is anti-hCG labeled antibody 42, wherein the label comprises a particle comprising a copolymer of methyl methacrylate and methacrylic acid having FeMe encapsulated therein.

Sample is placed on the test strip, wherein the sample is a urine sample that has or is suspected of having hCG. The urine naturally contains urea 45. As hCG flows through the first region 32, anti-hCG labeled monoclonal antibody 42 reacts with a first epitope of hCG, and binds thereto. The hCG bound with anti-hCG antibody continues to flow to the second region 34. An anti-hCG capture monoclonal antibody having biotin conjugated thereon is deposited at the second region 34. The capture antibody recognizes a different epitope of hCG, and binds thereto, forming a sandwich complex. The sandwich complex continues to flow to the third region 36.

The test line 36 comprises immobilized avidin 28 and deposited solulizable urease 44. Avidin 28 binds to the biotin that is conjugated to the capture antibody, which is bound to hCG with labeled antibody. Urea 45 present in urine reacts with urease 44 that becomes solubilized at the third region 36. Urease 44 hydrolyzes urea 45, producing carbon dioxide and ammonia. Ammonia reacts in aqueous solution to produce ammonium hydroxide 47, which results in a change in the local pH to an alkaline level. Increasing the pH causes the copolymer methyl methacrylate and methacrylic acid bead 42 to dissolve. FeMe 49 is released from the bead, producing electrochemical signals which are proportional to the concentration of hCG present in the urine, and which are detected by an electrode 50.

In these experiments, the working electrode is a gold wire and the reference electrode is a silver/silver chloride electrode. Both pierce the substrate transversely, perpendicular to the major faces of the substrate.

Figure 8:
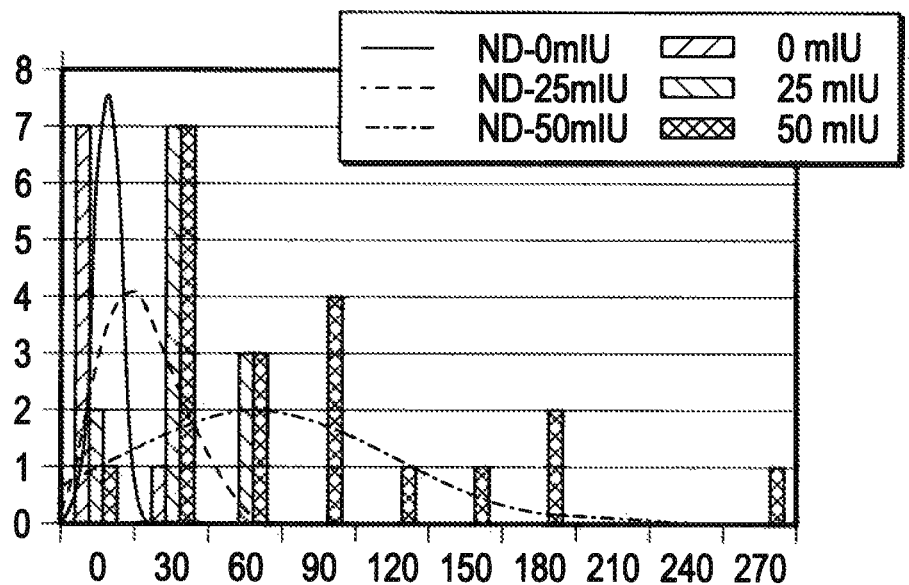
FIG. 8 provides a graphical representation of the data analysis of the electrochemical detection of human chorionic gonadotropin at various concentrations using the electrochemical LFA as described herein.

FIG. 8 provides a graphical representation of the data analysis of the electrochemical detection of hCG at various concentrations using the electrochemical LFA as described herein. The LFA strip was prepared as described above, comprising anti-hCG labeled antibody deposited thereon at a first position, anti-hCG biotin conjugated capture antibody deposited at a second position, and avidin and enzyme deposited at a test line. Samples of urine were prepared having various concentrations of hCG (0, 25, and 50 mIU/ml). Non-pregnant females typically have hCG urine levels at less than 5 mIU/ml, whereas levels greater than 5 mIU/mL are generally indicative of pregnancy. The various urine samples were applied to the test strip, and the electrochemical signal was detected. As seen in FIG. 8, the LFA is capable of differentiating between various concentrations of hCG. The bars represent individual responses, and the lines represent fitted normal distribution.

As one can appreciate, although the above examples demonstrate the principles of the electrochemical LFA in the context of hCG detection, the device is useful for the detection of any desirable analyte. The apparatus and method of the invention can be used as a tool to aid diagnosis and patient management. For example, the assay can be used to identify, confirm, or rule out disease in symptomatic patients, or to accurately prescribe therapeutic drugs and to monitor treatment, for example to monitor blood sugar levels in diabetic patients or to determine pregnancy. Other uses also include in epidemiology, where the rapid assay can be used to detect and monitor the incidence or prevalence of diseases for targeting and evaluating health programs, as well as in screening to determine the prevalence of disease in asymptomatic individuals.

While the foregoing is directed to aspects of the present disclosure, other and further aspects of the disclosure may be devised without departing from the basic scope thereof, and the scope thereof is determined by the claims that follow.

What is claimed is:

1. A diagnostic lateral flow assay device for detection of analyte in a sample, the device comprising:
   a substrate comprising:
   a first region comprising labeled antibodies specific for the analyte deposited thereon, wherein the labels of the labeled antibodies comprise enteric material particles comprising a copolymer of methyl methacrylate and methacrylic acid with ferrocene methanol embedded therein;
   a second region comprising avidin or antibodies specific for the analyte immobilized thereon and an enzyme deposited thereon, wherein the enzyme interacts with an enzyme substrate in or added to the sample during the detection process to cause the release of ferrocene methanol from enteric material particles bound in the second region; and a detector comprising at least one electrode surface to detect released ferrocene methanol.

2. The device of claim 1, wherein the enzyme substrate is naturally present in the sample.

3. The device of claim 1, wherein the enzyme is urease.

4. The device of claim 1, wherein the substrate comprises a material selected from the group consisting of cellulose, nitrocellulose, cellulose acetate, polyacrylamide, agarose polyacrylamide, copolymer, agarose, starch, nylon, nylon polyesters, dextran, cross-linked dextran, dextran acrylamide copolymer, cross-linked hydroxymethylmethacrylate, substituted cross-linked polystyrenes, polyvinylalcohol, wool, metal oxides, porous ceramics coated with hydrophilic organic polymers, and glass.

5. The device of claim 1, wherein the labels of the labeled antibodies have a diameter of between 40 nm and 300 nm.

6. The device of claim 1, wherein the at least one electrode surface is embedded in the substrate.

7. The device of claim 1, wherein the at least one electrode surface is formed by one or more wires extending transversely through the substrate perpendicular to the major faces of the substrate.

8. The device of claim 1, further comprising a current measurement circuit to convert the detection of the ferrocene methanol by the detector into a measurement indicative of concentration of analyte in the sample.

9. the device of claim 1, wherein if avidin is immobilized in the second region the substrate further comprises a third region between the first and second regions, and wherein the third region comprises biotinylated antibodies specific for the analyte deposited thereon.

10. A method of making a lateral flow assay device comprising:

mixing an entric material comprising a copolymer of methyl methacrylate and methacrylic acid with ferrocene methanol in a solvent;

removing the solvent to form particles of the enteric material having ferrocene methanol embedded therein;

attaching antibodies to the particles to produce labeled antibodies;

depositing the labeled antibodies onto a first region of solid matrix; and immobilizing avidin or antibodies specific for the analyte and depositing enzyme onto a second region of the solid matrix that reacts with an enzyme substrate in or added to an assay sample to release the embedded ferrocene methanol.

11. The method of claim 10, if avidin is immobilized in the second region, further comprising attaching biotin to antibodies specific for the analyte to produce biotinylated antibodies, and depositing the biotinylated antibodies onto a third region of the solid matrix.

12. A lateral flow assay method for determining the presence and quantity of analyte in a urine sample, the method comprising:

applying urine to the first region of the device in claim 1;

solubilizing labeled antibodies at a first region of the substrate with the urine, wherein the label of the labeled antibodies comprises an enteric material particle comprising a copolymer of methyl methacrylate and methacrylic acid having ferrocene methanol embedded therein;

solubilizing urease at a second region of the substrate with the urine to react with urea in the urine to raise the pH and release ferrocene methanol into the urine from labeled antibodies bound at the second region of the substrate;

detecting the released ferrocene methanol at the second region of the substrate; and determining the presence and amount of analyte in the sample based on the detected ferrocene methanol.

13. The method of claim 12, wherein the labeled antibodies bind to a first epitope of hCG, wherein the method additionally comprises solubilizing biotinylated antibodies with the urine at a third region of the substrate between the first region and the second region, wherein the biotinylated antibodies bind to a second different epitope of the hCG than the labeled antibodies, and wherein the second region of the substrate has avidin deposited thereon.

14. The method of claim 12, wherein the second region further comprises antibodies specific for the analyte immobilized thereon.

* * * * *